US006451813B1

(12) United States Patent
Cutler et al.

(10) Patent No.: US 6,451,813 B1
(45) Date of Patent: Sep. 17, 2002

(54) TREATMENT OF GASTROPARESIS IN CERTAIN PATIENT GROUPS

(75) Inventors: Neal R. Cutler, Los Angeles; John Sramek, Irvine, both of CA (US)

(73) Assignee: R. T. Alamo Ventures I, LLC, Beverly Hills, CA (US)

(*) Notice: Subject to any disclaimer, the term of this patent is extended or adjusted under 35 U.S.C. 154(b) by 0 days.

(21) Appl. No.: 09/771,077

(22) Filed: Jan. 26, 2001

(51) Int. Cl.[7] .............................................. A61K 31/44

(52) U.S. Cl. ..................................................... 514/312

(58) Field of Search ........................................ 514/312

(56) References Cited

U.S. PATENT DOCUMENTS

| | | | |
|---|---|---|---|
| 4,277,479 A | 7/1981 | Nishi et al. | 424/258 |
| 4,302,460 A | 11/1981 | Davies et al. | 424/258 |
| 4,522,884 A | 6/1985 | Brody | 428/400 |
| 4,552,891 A | 11/1985 | Ho et al. | 514/443 |
| 4,623,650 A | 11/1986 | Gilligan et al. | 514/312 |
| 4,710,506 A | 12/1987 | Davies et al. | 514/301 |
| 4,772,614 A | 9/1988 | Davies et al. | 514/312 |
| 4,855,291 A | 8/1989 | Davies | 514/312 |
| 4,877,793 A | 10/1989 | Davies | 514/301 |
| 4,997,840 A | 3/1991 | Davies et al. | 514/312 |
| 5,011,931 A | 4/1991 | MacLean et al. | 546/155 |
| 5,079,264 A | 1/1992 | MacLean et al. | 514/629 |
| 5,106,851 A | 4/1992 | Turconi et al. | 514/259 |
| 5,393,773 A | 2/1995 | Craig et al. | 514/415 |
| 5,437,291 A | 8/1995 | Pasricha et al. | 128/898 |
| 5,554,639 A | 9/1996 | Craig et al. | 514/415 |
| 5,627,191 A | 5/1997 | Birch et al. | 514/303 |
| 5,733,917 A | 3/1998 | Ohuchi et al. | 514/299 |
| 5,753,673 A | 5/1998 | Ohuchi et al. | 514/304 |
| 5,801,161 A | 9/1998 | Merkus | 514/52 |
| 5,864,037 A | 1/1999 | Chasin et al. | 544/118 |
| 5,869,479 A | 2/1999 | Kreutner et al. | 514/212 |
| 5,955,477 A | 9/1999 | Gray et al. | 514/327 |
| 5,955,478 A | 9/1999 | Gray et al. | 514/327 |
| 6,114,304 A | 9/2000 | Kolterman et al. | 514/12 |

FOREIGN PATENT DOCUMENTS

| | | |
|---|---|---|
| WO | WO 99/42095 | 8/1999 |
| WO | WO 99/64055 | 12/1999 |
| WO | WO 99/07595 | 2/2000 |

OTHER PUBLICATIONS

McMurry, *Organic Chemistry*, 2nd Ed., Brooks/Cole Publishing, Belmont, CA (1988), pp. 1044–1045 and 1076.

Kelso et al. "Actions of the Novel Vasodilator, Flosequinan, in Isolated Ventricular Cardiomyocytes," *J. Cardiovasc. Pharmacol.* 25:376–386 (1995).

Perreault et al., "Differential inotropic effects of flosequinan in ventricular muscle from noemal ferrets versus patients with end–stage heart failure," *Br. J. Pharmacol.* 106:511–516 (1992).

Jones et al., "Effect of flosequinan on ischaemia–induced arrhythmias and on ventricular cyclic nucleotide content in the anaestetized rat," *Br. J. Pharmacol.* 108:1111–1116 (1993).

Gristwood et al., "Studies on the cardiac actions of flosequinan in vitro," *Br. J. Pharmacol.* 105:985–991 (1992).

Frodsham et al., "Effect of flosequinan upon isoenzymes of phosphodiesterase from guinea–pig cardiac and vascular smooth muscle," *Eur. J. Pharmacol.* 211:383–391 (1992).

Dawson et al., "Cilostazol Has Beneficial Effects in Treatment of Intermittent Claudication," *Circulation* 98:678–686 (1998).

Elàm et al., "Effect of the Novel Antiplatelet Agent Cilostazol on Plasma Lipoproreins in Patients with Intermittent Claudication," *Arterioscler. Thromb. Vasc. Biol.* 18:1942–1947 (1998).

Drug Evaluation Monographs, vol. 99, Micromedex Inc. (1999).

Nishi et al., "Studies on 2–Oxoquinoline Derivatives as Blood Platelet Aggregation Inhibitors. II. 6–[3–(1–Cyclohexyl–5–tetrazolyl)propoxy]–1, 2–dihydro–2–oxoquinoline and Related Compounds," *Chem. Pharm. Bull.* 31:1151–1157 (1983).

Shimizu, T. et al., "Physico–chemical Properties and Stability of Cilostazol," *Arzneim–Forsch.* 35:1117–1208 (1985).

Suri et al., "Pharmacolinetics of Multiple–Dose Oral Cilostazol in Middle–Age and Elderly Men and Women," *J. Clin. Pharmacol.* 38:144–150 (1998).

Niki and Mori, "Phase I Study od Cilostazol," *Arzneim.–Forsch* 35:1173–1185 (1985).

Watkins, CC et al. "Insulin restores neuronal nitric oxide synthase expression and function that is lost in diabetic gastropathy" *J Clin Invest* 106:373–384 (2000).

Moreira et al., "Side–effect profile of sildenafil citrate (Viagra) in clinical practice," *Urology,* 56(3):474–76 (2000).

Winslow R. "Viagra Could Treat Disorder in Diabetics" Wall Street Journal, Aug. 1, 2000.

Lewis H.M. et al. "A comparison of the metabolic effects of flosequinan and propanolol in patients with non–insulin–dependent diabetes mellitus". *J Clin Pharm Ther* 16:161–166 (1991).

Koch KL. "Diabetic Gastropathy. Gastric neuromuscular dysfunction in diabetes mellitus. A review of symptoms, pathophysiology, and treatment". *Digestive Diseases and Sciences* 44:1061–1075 (1999).

Richter J.E. "Cisapride: Limited access and alternatives". *Cleve Clin J Med* 67: 471–472 (2000).

(List continued on next page.)

Primary Examiner—Rebecca Cook
(74) Attorney, Agent, or Firm—Medlen & Carroll, LLP (57) ABSTRACT

Methods for treating specific patient groups for gastroparesis are provided. The methods of the present invention comprise the utilization of pharmaceutical compositions comprising quinolinones (and derivatives) in patients with symptoms of gastroparesis who are otherwise free of cardiac disease and/or who have not been given organic nitrates.

18 Claims, 2 Drawing Sheets

OTHER PUBLICATIONS

Brown C.K. and Khanderia U. "Use of metoclopramide, domperidone, and cisapride in the management of diabetic gastroparesis". *Clin Pharm* 9:357–365 (1990).

Evans A.J. and Krentz A.J. "Should cisapride be avoided in patients with diabetic gastroparesis?". *J Diabetes Complications* 13:314–315 (1999).

Rosa–E–Silva L. et al. "Treatment of diabetic gastroparesis with oral clonidine". *Aliment Pharmacol Ther* 9: 179–183 (1995).

Dumitrascu D.L. and Weinbeck M. "Domperidone versus Metaclopramide in the Treatment of Diabetic Gastroparesis". *AJG* 95: 316–317 (2000).

Mansi C. et al., "Gastrokinetic Effects of Levosulpiride in Dyspeptic Patients with Diabetic Gastroparesis". *Am. J. Gastroenterology* 90: 1989–1993 (1995).

Annese V. et al. "Cisapride and erythromycin prokinetic effects in gastroparesis due to type 1 (insulin–dependent) diabetes mellitus". *Aliment Pharmacol. Ther* 11:599–603 (1997).

Jones K.L. et al. "Effects of fedotozine on gastric emptying and upper gastrointestinal symptoms in diabetic gastroparesis". *Aliment Pharmacol Ther* 14:937–943 (2000).

Suh K.S. et al., "Effect of Cilostazol on the Neuropathies of Streptozotocin–Induced Diabetic Rats" *Korean Journal of Internal Medicine* 14:34–40 (1999).

Hasler W.L. et al., "Mediation of Hyperglycemia–Evoked Gastric Slow–Wave Dysrhythmias by Endogenous Prostaglandins" *Gastroeneterology* 108:727–736 (1995).

Saur D. et al., "Distinct Expression of Splice Variants of Neuronal Nitric Oxide Synthase in the Human Gastrointestinal Tract" *Gastroenterology* 118:849–858 (2000).

Hornbuckle H. and Barnett J.L., "The Diagnosis of and Work–up of the Patient With Gastroparesis". *J Clin Gastroenterol* 30:117–124 (2000).

National Digestive Diseases Information Clearinghouse. "Gastroparesis and Diabetes". http://www.niddk.nih.gov/health/digest/pubs/gastro/gastro.htm (Posted May 1999; e–text updated Apr. 2000).

Jackson Gastroenterology "Gastroparesis"http://www.gi-care.com/pated/ecdgs45.htm. Copyright date 1998.

Latham EJ and Stanforth SP. "Synthesis of indoles and quinolones by sequential Wittig and Heck reactions", *J. Chem. Soc., Perkin Trans.* 1:2059–2063 (1997).

Meth–Cohn O and Taylor DL., "The Reverse Vilsmeier Approach to the Synthesis of Quinolines, Quinolinium Salts and Quinolones", *Tetrahedron* 51:12869–12882 (1995).

Stadlbauer W., "Methods for the synthesis of 4–azido–2(1H)–quinolones", *Monatshefte für Chemie* 117:1305–1323 (1986).

Radl S and Bouzard D., "Recent advances in the synthesis of antibacterial quinolones", *Heterocycles* 34:2143–2177 (1992).

Dutta U. et al., "Double blind controlled trial of cisapride on gastric emptying in diabetics". *Trop. Gastroeneterol* 20:116–119 (1999) [abstract only].

Ikezono et al., "General Pharmacological Properties of the New Vasodilator Flosequinan" *Arzheim–Forsch/ Drug Res* 42 (II) (10):1200–1211 (1992).

TREATMENT OF GASTROPARESIS IN CERTAIN PATIENT GROUPS

FIELD OF THE INVENTION

The present invention relates to methods for the treatment of gastroparesis in males and females in particular treatment groups, such as diabetics. The methods of the present invention comprise the utilization of pharmaceutical compositions to patients who are free of symptoms of cardiac disease and who have not been treated with drugs which cause hypotensive effects, such as nitrites and nitrates.

BACKGROUND

Gastroparesis, or delayed stomach emptying, is most often a complication of diabetes. Seven million people in the United States may be affected by diabetes, and up to 75% of diabetic patients may experience gastrointestinal dysfunction, including diabetic gastroparesis, a syndrome of delayed gastric emptying, leading to nausea, vomiting, abdominal pain and early satiety.

There is more than one cause of gastroparesis. Although diabetes is the most common known cause, gastroparesis can be the result of physical problems, medications, as well as metabolic, smooth muscle and nervous system disorders. For example, physical problems leading to gastroparesis can include scarring from tumors and ulcers, as well as surgery on the vagus nerve or stomach. Certain medications, including Cardizem and other calcium blockers, which slow contractions in the intestine or weaken the stomach, can contribute to gastroparesis. Hypothyroidism is an example of a metabolic disorder associated with gastroparesis. Smooth muscle disorders such as amyloidosis and scleroderma can cause gastroparesis, as can disorders of the nervous system, such as Parkinson's disease and abdominal migraine, a syndrome characterized by recurrent sterotypic episodes of paroxysmal abdominal pain and nausea and/or vomiting.

In addition to symptoms such as nausea, vomiting, an early feeling of fullness when eating, weight loss, abdominal bloating and discomfort, gastroparesis can lead to several complications. For example, if food lingers too long in the stomach, it can cause problems like bacterial overgrowth from the fermentation of food. Also, the food can harden into solid masses called bezoars, that may cause nausea, vomiting, and obstruction in the stomach. Bezoars can be dangerous if they block the passage of food into the small intestine. In diabetic patients, gastroparesis can make diabetes worse by adding to the difficulty of controlling blood glucose. When food that has been delayed in the stomach finally enters the small intestine and is absorbed, blood glucose levels rise. Since gastroparesis makes stomach emptying unpredictable, a person's blood glucose levels can be erratic and difficult to control. High blood glucose causes chemical changes in nerves and damages the blood vessels that carry oxygen and nutrients to the nerves. This can damage the vagus nerve, potentially leading to symptoms of gastroparesis, if blood glucose levels remain high over a long period of time.

Some of the treatments available to help manage gastroparesis include meal and food changes. A patient may be asked to eat six small meals a day, rather than three large ones. Several liquid meals a day may be recommended until the gastroparesis is corrected. Avoiding fatty and high-fiber foods may also be recommended, as fat naturally slows digestion and some high-fiber foods like oranges and broccoli contain material that cannot be digested. The indigestible part will remain in the stomach too long and possibly form bezoars.

If other approaches do not work, a patient may need surgery to insert a feeding tube. The tube is inserted through the skin on the abdomen into the small intestine. This allows nutrients to be put directly into the small intestine, bypassing the stomach altogether. A feeding tube can be temporary and is used only if necessary when gastroparesis is severe. As an alternative to a feeding tube, parenteral nutrition may be delivered. A catheter is inserted in a chest vein, leaving an opening outside the skin. For feeding, a bag containing liquid nutrients or medication is attached to the catheter, and fluid enters the bloodstream through the vein. This bypasses the digestive system when gastroparesis is severe and not helped by other methods.

In diabetic patients with gastroparesis, food is being absorbed more slowly and at unpredictable times. These patients may need to take insulin more often, take insulin after eating, rather than before, and check blood glucose levels frequently after eating, administering insulin whenever necessary.

These treatments clearly involve inconvenience to the patient, turning eating and mealtimes into challenges. In the cases of feeding tubes or catheters, surgical intervention may be associated with risks and complications that can accompany any surgery. What is needed is an intervention that is effective and less disruptive to the patient while lacking in significant side effects.

SUMMARY OF THE INVENTION

The present invention provides methods for the treatment of gastroparesis in males and females in particular treatment groups, including diabetics. The methods of the present invention comprise the utilization of pharmaceutical compositions to patients who are free of symptoms of cardiac disease and who have not been treated with drugs which cause hypotensive effects, such as nitrites and nitrates. The compositions comprise quinolinones, including derivatives thereof. Quinolinones are also known as quinolones and oxo-quinolines.

It is not intended that the present invention be limited by the nature of the derivative. In one embodiment, the quinolinone derivative is cilostazol (6-[4-(1-cyclohexyl-1H-tetrazol-5-yl)butoxy]-3,4-dihydro-2(1H)-quinolinone; 6-[4-(1-cyclohexyl-1H-tetrazol-5-yl)butoxy]-3,4-dihydrocarbostyril; 3,4-Dihydro-6-(4-(1-cyclohexyl-1H-tetrazol-5-yl)butoxy)-2(1H)-quinolinone).

In yet other embodiments, metabolites of cilostazol are contemplated for use in the methods of the presently claimed invention. Metabolites of cilostazol include, but are not limited to monohydroxycilostazol, monohydroxydehydrocilostazol, 3,4-dihydro-6-hydroxy-2(1H)-quinolinone, their conjugates and dehydrocilostazol.

In another embodiment, the present invention contemplates halogenated quinolinones (e.g., fluoroquinolinone). In a preferred embodiment, the quinolinone is a thioquinolinone or a sulphinyl or suphonyl derivatives thereof. In one embodiment, the halogenated quinolinone is flosequinan [(−)-7-fluoro-1-methyl-3-(methyl-sulphinyl)-4(1H)-quinolinone]; [7-Fluoro-1-methyl-3-(methylsulfinyl)-4(1H)-quinolone]. In a preferred embodiment, an enantiomer of flosequinan is used.

In one embodiment, the present invention contemplates a method, comprising: a) providing: i) a male or female with symptoms of gastroparesis, and ii) a composition comprising a quinolinone selected from the group consisting of a racemic mixture of flosequinan and an enantiomer of flosequinan; and b) administering said composition to said male or female (e.g. such that said symptoms are reduced). It is not intended that the present invention be limited to particular symptoms of gastroparesis. A variety of such symptoms are contemplated, including but not limited to, nausea, early satiety, postprandial bloating and fullness, and vomiting. In one embodiment, the present invention contemplates administering said flosequinan to said male or female under conditions such that symptoms of said male or female are improved.

In another embodiment, the present invention contemplates a method, comprising: a) providing: i) a male or female with symptoms of gastroparesis, and ii) cilostazol; and b) administering said cilostazol to said male or female (e.g. such that said symptoms are reduced). It is not intended that the present invention be limited to particular symptoms of gastroparesis. A variety of such symptoms are contemplated, including but not limited to, nausea, early satiety, postprandial bloating and fullness, and vomiting. In one embodiment, the present invention contemplates administering said cilostazol to said male or female under conditions such that symptoms of said male or female are improved.

It is not intended that the present invention be limited by the method of introduction of flosequinan or cilostazol. In one embodiment, the flosequinan or cilostazol are introduced into said male or female orally.

In a preferred embodiment, the male or female is an adult human and the oral dosage of flosequinan is in a single dose per day of up to approximately two hundred milligrams, and more preferably, between approximately twenty-five to approximately seventy-five milligrams. In another preferred embodiment, flosequinan is administered in a single oral dose per day of between approximately one hundred and twenty-five and approximately two hundred milligrams. In another preferred embodiment, the male or female is an adult human and the oral dosage of flosequinan is in three daily doses, before meals, each of up to approximately two hundred milligrams. In another embodiment, each of the three daily doses is between approximately twenty-five to approximately seventy-five milligrams. In another embodiment, flosequinan is administered in three oral doses per day, before meals, each dose being between approximately one hundred and twenty-five and approximately two hundred milligrams.

In another embodiment, the male or female is an adult human and the oral dosage comprises a purified enantiomer of flosequinan. In one embodiment, the oral dosage of a purified enantiomer of flosequinan is in a single dose per day of up to approximately two hundred milligrams, and more preferably between approximately fifty to approximately seventy-five milligrams. In another preferred embodiment, a purified enantiomer of flosequinan is administered in a single oral dose per day of between approximately twenty and approximately fifty, and even more preferably, between approximately ten and approximately twenty milligrams per day. In another embodiment, the male or female is an adult human and the oral dosage of a purified enantiomer of flosequinan is in three daily doses, before meals, each of up to approximately two hundred milligrams. In another embodiment, each of the three daily doses is between approximately one hundred and twenty-five to approximately two hundred milligrams, and in another embodiment, each of the three daily doses is between approximately fifty to approximately seventy-five milligrams, and in yet another embodiment, each of the three daily doses is between approximately twenty and approximately fifty milligrams. In another embodiment, each of the three daily doses is between approximately ten and approximately twenty milligrams.

In a preferred embodiment, the male or female is an adult human and the oral dosage of cilostazol is in a single dose per day of up to approximately two hundred milligrams, and more preferably, between approximately twenty-five to approximately one hundred milligrams. In an even more preferred embodiment, cilostazol is administered in two oral doses per day of between approximately fifty and approximately one hundred milligrams. In another preferred embodiment, the male or female is an adult human and the oral dosage of cilostazol is in three daily doses, before meals, each of up to approximately two hundred milligrams. In another embodiment, each of the three daily doses is between approximately twenty-five to approximately seventy-five milligrams, and in yet another embodiment, each of the three daily doses is between approximately fifty to approximately one hundred milligrams.

In other embodiments said flosequinan or cilostazol is introduced cutaneously, by standard injection or intranasally.

In one embodiment, the method comprises a) providing: i) a patient (whether male or female) suffering from symptoms of gastroparesis who is free from cardiac disease; and ii) flosequinan; and b) introducing said flosequinan to said patient such that such symptoms are reduced.

In another embodiment, the method comprises a) providing: i) a patient (whether male or female) suffering from symptoms of gastroparesis who is not being treated (and/or has not been treated in the past) with a drug that causes hypotensive effects, and ii) flosequinan; and b) introducing said flosequinan to said patient such that such symptoms are reduced.

In another embodiment, the method comprises a) providing: i) a patient (whether male or female) suffering from symptoms of gastroparesis who is not being treated (and/or has not been treated in the past) with a nitrite or nitrate, and ii) flosequinan; and b) introducing said flosequinan to said patient such that such symptoms are reduced.

In one embodiment, the method comprises a) providing: i) a patient (whether male or female) suffering from symptoms of gastroparesis who is free from cardiac disease, including, but not limited to, congestive heart failure; and ii) cilostazol; and b) introducing said cilostazol to said patient such that such symptoms are reduced.

In another embodiment, the method comprises a) providing: i) a patient (whether male or female) suffering from symptoms of gastroparesis who is not being treated (and/or has not been treated in the past) with a drug that causes hypotensive effects, and ii) cilostazol; and b) introducing said cilostazol to said patient such that such symptoms are reduced.

In another embodiment, the method comprises a) providing: i) a patient (whether male or female) suffering from symptoms of gastroparesis who is not being treated (and/or has not been treated in the past) with a nitrite or nitrate, and ii) cilostazol; and b) introducing said cilostazol to said patient such that such symptoms are reduced.

The present invention also contemplates the use of a pharmaceutical composition to treat diabetic patients with symptoms of gastroparesis. For example, one embodiment comprises a) providing: i) a male or female subject with diabetes, and ii) flosequinan; and b) introducing said flosequinan to said subject with diabetes such that the condition of said subject is improved.

The present invention also contemplates the use of a pharmaceutical composition to treat diabetic patients with symptoms of gastroparesis. For example, one embodiment comprises a) providing: i) a male or female subject with diabetes, and ii) cilostazol; and b) introducing said cilostazol to said subject with diabetes such that the condition of said subject is improved.

It is not intended that the present invention be limited by the nature of the formulation. In one embodiment, the present invention contemplates a formulation comprising a quinolone or quinolinone or derivative thereof in a mixture comprising lactose.

DEFINITIONS

As used herein, the term "quinolinone" refers to chemical compositions comprising quinolinone as set forth in the following structure (2-quinolone):

as well as other forms of quinolinone, (e.g., isoquinolone):

As used herein, the phrase "derivatives of quinolinone" refers to chemical compositions comprising quinolinone with a chemical group attached, including (but not limited to) halogenated quinolinone.

As used herein, the phrase "methylsulphinyl derivatives of quinolinone" refers to chemical compositions comprising quinolinone with a methylsulphinyl group attached. Examples include flosequinan (7-fluoro-1-methyl-3-(methylsulphinyl)-4(1H)-quinolone; 7-fluoro-1-methyl-3-(methylsulfinyl)-4(1H)-quinolinone):

and sulfone metabolites of flosequinan:

Other examples of quinolinone derivatives include cilostazol (6-[4-(1-cyclohexyl-1H-tetrazol-5-yl)butoxy]-3,4-dihydro-2(1H)-quinolinone; 6-[4-(1-cyclohexyl-1H-tetrazol-5-yl)butoxy]-3,4-dihydrocarbostyril; [3,4-Dihydro-6-(4-(1-cyclohexyl-1H-tetrazol-5-yl)butoxy)-2(1H)-quinolinone)]:

and metabolites of cilostazol. Examples include monohydroxycilostazol, monohydroxydehydrocilostazol, 3,4-dihydro-6-hydroxy-2(1H)-quinolinone, their conjugates and dehydrocilostazol.

As used herein, a patient who is "free from cardiac disease" and a patient who is "free from symptoms of cardiac disease" indicate that the patient has not been diagnosed with angina, myocardial infarction, congestive heart failure and that symptoms of angina, ischemia, myocardial infarction, congestive heart failure have not been detected, respectively.

As used herein, "drugs that have hypotensive effects" are those drugs which, when administered, cause the patient's end-diastolic blood pressure to be reduced. Nitrates are commonly used drugs which have hypotensive effects.

As used herein, "nitrates" are compounds that contain the —$NO_3$—moiety. Nitrates typically used in the clinic are shown in Table 1.

As used herein, "nitrites" are compounds that contain the —$NO_2$—moiety. Nitrites typically used in the clinic are shown in Table 1.

As used herein "standard injection" refers to the placement of a pharmaceutical composition into a subject (e.g., with a hypodermic needle). For example, such injection can be made subcutaneously, intravenously, intramuscularly, intracavernosally, etc.

As used herein, "by oral administration" refers to the introduction of a pharmaceutical composition into a subject by way of the oral cavity (e.g., in aqueous liquid or solid form).

As used herein, "cutaneously" refers to the introduction of a pharmaceutical composition into a subject by application to the surface of the skin such that the composition is absorbed into the subject.

As used herein, "intranasally" refers to the introduction of a pharmaceutical composition within the nasal cavity.

As used herein, "respiratory inhalation" refers to the introduction of a pharmaceutical composition within the respiratory tract.

As used herein "single dosage" refers to a pharmaceutical composition of a formulation that is capable of achieving its intended effect in a single application or administration.

templates treatment such that symptoms are reduced (and the condition of the patient is thereby "improved"), albeit not completely eliminated.

As used herein, "diabetes" refers to a disease in which the body does not produce or properly use insulin, or does not produce sufficient amounts of insulin.

TABLE 1

| NONPROPRIETARY NAMES AND TRADE NAMES | CHEMICAL STRUCTURE | PREPARATIONS, USUAL DOSES, AND ROUTES OF ADMINISTRATION* |
|---|---|---|
| Amyl nitrite (isoamyl nitrite) |  | Inh: 0.18 or 0.3 ml, inhalation |
| Nitroglycerin (glyceryl trinitrate; NITRO-BID, NITROSTAT, NITROL, NITRO-DUR, others) |  | T: 0.15 to 0.6 mg as needed<br>S: 0.4 mg per spray as needed<br>C: 2.5 to 9 mg two to four times daily<br>B: 1 mg every 3 to 5 h<br>O: 1.25 to 5 cm (½ to 2 in.), topically to skin every 4 to 8 h<br>D: 1 disc (2.5 to 15 mg) every 24 h<br>IV: 5 μg/min; increments of 5 μg/min |
| Isosorbide dinitrate (ISORDIL, SORBITRATE, DILATRATE, others) |  | T: 2.5 to 10 mg every 2 to 3 h<br>T(C): 5 to 10 mg every 2 to 3 h<br>T(O): 10 to 40 mg every 6 h<br>C: 40 to 80 mg every 8 to 12 h |
| Isosorbide-5-mononitrate (IMDUR, ISMO, others) |  | T: 10 to 40 mg twice daily<br>C: 60 mg daily |
| Erythrityl tetranitrate (CARDILATE) |  | T: 5 to 10 mg as needed<br>T(O): 10 mg three times daily |

B buccal (transmucosal) tablet;
C, sustained-release capsule or tablet;
D, transdermal disc;
Inh, inhalant;
IV, intravenous injection;
O, ointment;
S, lingual spray;
T, tablet for sublingual use;
T(C), chewable tablet;
T(O), oral tablet or capsule.

As used herein, "symptoms of gastroparesis" refers to any two of the following symptoms: nausea, vomiting, early satiety, abdominal bloating, abdominal discomfort and weight loss, as a result of delayed gastric emptying. Symptoms are "reduced" when the magnitude (e.g. intensity) or frequency of symptoms is reduced. It is not intended that the present invention be limited only to cases where the symptoms are eliminated. The present invention specifically con- As used herein, the term "enantiomer" refers to stereoisomers of molecules that are non-superimposable mirror images of each other. Enantiomers have identical physical properties, such as melting points and boiling points, and also have identical spectroscopic properties. Enantiomers differ from each other with respect to their interaction with plane-polarized light and with respect to their biological activity.

As used herein, the term "stereoisomer" refers to compounds that have their atoms connected in the same order but differ in the arrangement of their atoms in space. (e.g. cis-2-butane and trans-2-butane).

As used herein, the terms "purified enantiomer" and "purified enantiomer preparation" are meant to indicate a preparation (e.g. derived from a racemic mixture) wherein one enantiomer has been enriched over the other, and more preferably, wherein the other enantiomer represents less than 10%, and more preferably less than 5%, and still more preferably, less than 2% of the preparation.

As used herein, the term "racemic mixture" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The terms "lower alkyl", "lower alkoxy", "lower alkanoyl", and "lower alkythio" denote such groups containing 1–8 carbon atoms, especially 2–4 carbon atoms for lower alkanoyl and 1–4 carbon atoms for the other groups. Examples of such groups include methyl, ethyl, propyl, isopropyl, n-butyl, isobutyl, tert-butyl, n-heptyl, n-octyl, methoxy, ethoxy, propoxy, n-butoxy, isobutoxy, acetyl, propionyl, butyryl, methylthio, ethylthio, propylthio and n-butylthio.

As used hereinafter, the term "active compound" denotes a pyridinone compound of general formula I (as illustrated and described below in the section entitled "Other Compounds Useful In The Treatment of Gastroparesis"), or a quinolinone or quinolinone derivative as illustrated and described above.

As used herein, the term "diastereoisomers" refers to stereoisomers that are not mirror images of each other.

As used herein, the term "subject" refers to both humans and animals.

DETAILED DESCRIPTION OF THE INVENTION

Figure 1:
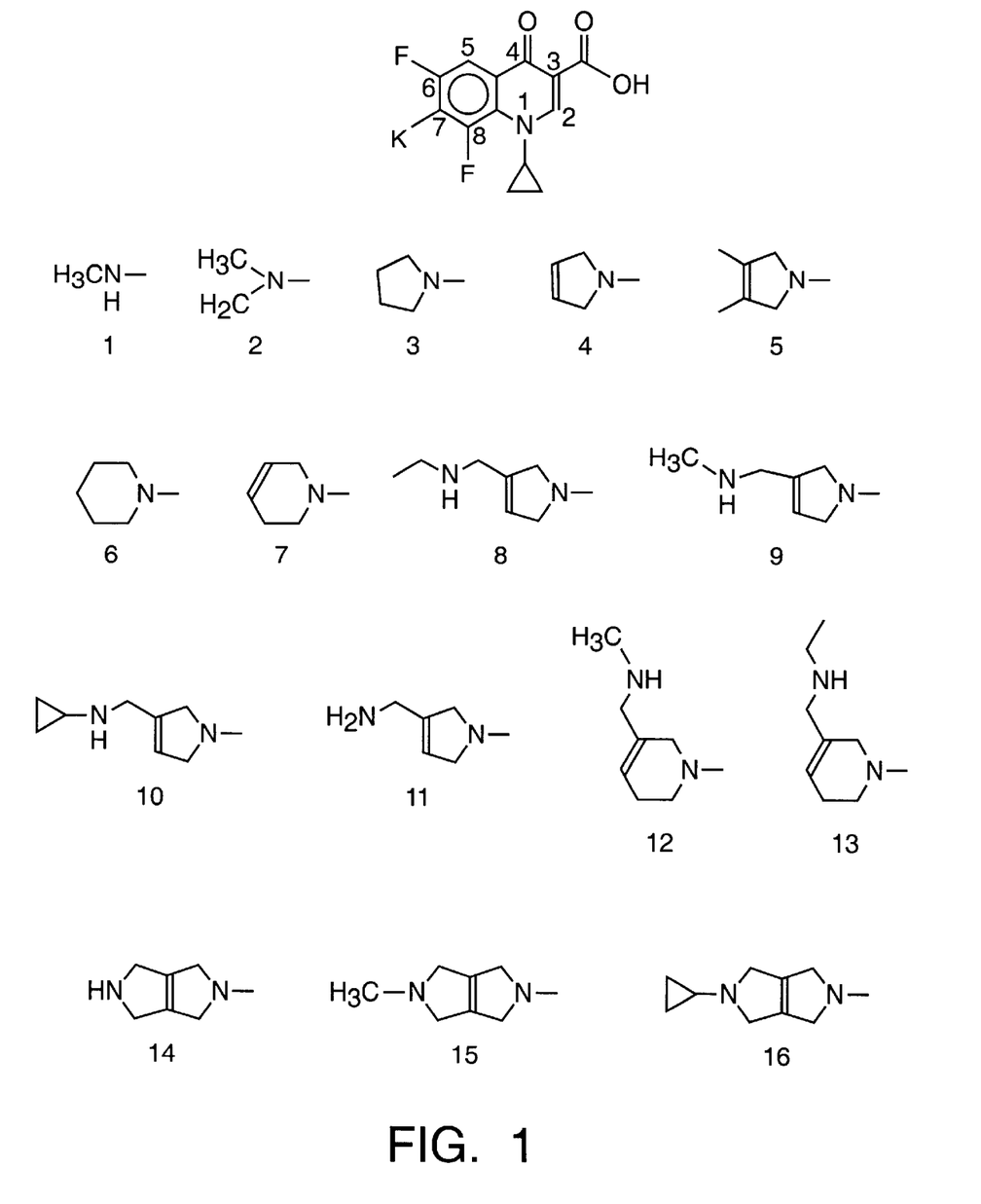
FIG. 1 depicts the chemical structure of a quinolinone (top) and 16 C-7 substituents (bottom).

The present invention provides methods for the treatment of gastroparesis in males and females (including but not limited to gastroparesis in patients with diabetes) in particular treatment groups. The methods of the present invention comprise the utilization of pharmaceutical compositions to patients who are free of symptoms of cardiac disease and who have not been treated with drugs which cause hypotensive effects, such as nitrites and nitrates. The compositions comprise quinolinones and derivatives thereof. A variety of quinolinone derivatives are shown in FIG. 1. Methods for producing antibiotic derivatives of a particular quinolone carboxylic acid skeleton are provided in U.S. Pat. No. 4,623,650 to Gilligan et al., herein incorporated by reference.

In one embodiment, racemic flosequinan or an enantiomer of flosequinan is administered. Importantly, flosequinan may potentiate the hypotensive effects of nitrates, and its administration to patients who are concurrently using organic nitrates in any form may be contraindicated.

In one embodiment, the present invention contemplates the use of compositions that are effective to reduce or improve the symptoms of gastroparesis. The compositions utilized in the methods of the present invention comprise quinolinones and derivatives thereof.

While the present invention is not limited by the nature of the derivatives, in one embodiment, the present invention encompasses the use of a variety of quinolinone derivatives. One skilled in the art can readily produce such derivatives as set forth in McMurry, Organic Chemistry 2nd Ed., Brooks/Cole Publishing, Belmont, Calif. (1988), pages 1044–1045 and 1076.

In another embodiment, the present invention contemplates the use of methylthio and methylsulphinyl derivatives of quinolinone. In a preferred embodiment, the methylsulphinyl derivative is flosequinan (whether as a racemic mixture or as a purified enantiomer).

Methods of producing methylsuphinyl and methylthio derivatives of quinolone, including flosequinan, are set forth in U.S. Pat. Nos. 5,079,264 and 5,011,931 to MacLean et al., hereby incorporated by reference.

The action of flosequinan in the body is not precisely understood and the present invention is not limited to any particular mechanism of action. Its activity in the body is attributed to flosequinan itself, as well as its sulfone metabolite. It has been reported to be useful to some degree in the treatment of heart failure. [See Kelso et al., J Cardiovasc. Pharmacol. 25:376 (1995)]. However, its action appears to have little effect in patients with end-stage failure [Perreault et al., Br. J Pharmacol. 106:511 (1992)] and does not affect mortality or arrhythmias following coronary artery ligation [Jones et al., Br. J Pharmacol. 108:1111 (1993)].

Likewise, flosequinan has been reported to be a selective inhibitor of phosphodiesterase III [Gristwood et al., Br. J Pharmacol. 105:985 (1992)]. [Frodsham et al., Eur. J Pharmacol. 211:383 (1992)], however, report that the phosphodiesterase inhibition of flosequinan, as relevant to its efficacy in heart failure, is questionable. Thus, the application of flosequinan to particular purposes in the body is not well-characterized and must be determined empirically.

Cilostazol is a phosphodiesterase inhibitor (type III) that suppresses platelet aggregation and also acts as a direct arterial vasodilator. In addition to its reported vasodilator and antiplatelet effects, cilostazol has been proposed to have beneficial effects on plasma lipoproteins, increasing plasma high density lipoprotein cholesterol and apoliproprotein (See e.g., Dawson et al., Circulation 98: 678–686 [1998]; Elam et al., Arterioscler Thromb. Vasc. Biol. 18: 1942–1947 [1998]; Drug Evaluation Monographs, vol. 99, Micromedex Inc.).

Methods of preparation of cilostazol are set forth by Nishi et al. (Chem. Pharm. Bull. 31: 1151 [1983], and U.S. Pat. No. 4,277,479, hereby incorporated by reference), and its pharmacology, metabolism, mechanism of action and clinical evaluations are described in Arzneimittel-Forsch. 35: 1117–1208 (1985), hereby incorporated by reference.

Diagnosis of Gastroparesis

Determination whether a patient is suffering from gastroparesis is readily made by a person skilled in the art using a number of readily available diagnostic procedures. A barium X-ray is commonly used to diagnose gastroparesis. After fasting for 12 hours, the patient drinks a thick liquid containing barium. In the normal situation, the barium detected by X-ray after 12 hours of fasting should reveal an empty stomach. If the X-ray shows food in the stomach, gastroparesis is likely. A similar technique to diagnose gastroparesis is through the barium beefsteak meal. In this case, the patient eats a meal that contains barium, thus allowing the radiologist to monitor the stomach as the meal is digested. The amount of time that it takes for the barium meal to be digested and leave the stomach is an indication of how well the stomach is working.

A radioisotope gastric-emptying scan can also be employed. In this test, the patient eats food (usually scrambled eggs or a stew) that contains a radioisotope. After eating, the radioisotope can be detected as the food leaves the stomach. Gastroparesis is diagnosed if more than half the food remains in the stomach after two hours.

A gastric manometry test measures electrical and muscular activity in the stomach. A thin tube is passed down the throat into the stomach. The tube contains a thin wire that takes measurements of the stomach's electrical and muscular activity as it digests liquid and solid food. An electrogastrogram (EGG) is a noninvasive procedure that can be used to measure the electrical waves that normally sweep over the stomach and precede each contraction.

Other tests can rule out causes of gastroparesis other than diabetes. These tests include upper endoscopy and ultrasound to examine the lining and possible physical obstructions of the stomach and rule out gallbladder disease and pancreatitis.

Treatment of Gastroparesis

It is not intended that the present invention be limited by the particular nature of the therapeutic preparation. For example, the quinolinones or quinolinone derivatives (e.g. flosequinan or cilostazol) can be provided together with physiologically tolerable liquid, gel or solid carriers, diluents, adjuvants and excipients. In addition, quinolinone analogs may be used together with other chemotherapeutic agents. On the other hand, formulations may also contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The present invention is not limited by the method of introduction of the therapeutic compound to the body. Among other methods, the present invention contemplates administering cutaneously, orally, or by standard injection (e.g intravenous).

The present invention also contemplates administering flosequinan or cilostazol to the patient intranasally or through respiratory inhalation. Formulations suitable for intranasal administration include ointments, creams, lotions, pastes, gels, sprays, aerosols, oils and other pharmaceutical carriers which accomplish direct contact between flosequinan or cilostazol or a pharmaceutical composition comprising flosequinan or cilostazol and the nasal cavity. Examples of pharmaceutical compositions administered intranasally are described in U.S. Pat. Nos. 5,393,773 and 5,554,639 to Craig et al.; and 5,801,161 to Merkus, all hereby incorporated by reference. Formulations suitable for respiratory inhalation include ointments, creams, lotions, pastes, gels, sprays, aerosols, oils and other pharmaceutical carriers which accomplish direct contact between flosequinan or cilostazol or a pharmaceutical composition comprising flosequinan or cilostazol and the respiratory tract. Examples of pharmaceutical compositions administered through respiratory inhalation are described in U.S. Pat. No. 4,552,891 to Hu et al.; 5,869,479 to Kreutner et al., and 5,864,037 to Chasis et al., all hereby incorporated by reference.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacologic agents to patients can be accomplished via aerosolization. Alternatively, the agent may be administered to the lung through a bronchoscope. Of course, the therapeutic agents may be investigated for their efficacy via other routes of administration, including parenteral administration.

Oral administration of flosequinan is an effective mode of administration, with a mean absolute bioavailability of 72% following a single dose of fifty milligrams. Peak plasma concentrations of flosequinan are observed 1–2 hours following oral administration, while peak metabolite plasma levels are observed about seven hours following oral dosage. While the present invention is not limited to a specific dosage level, for adult humans, in one preferred embodiment the dosage is a single dosage per day of 25 milligrams, while in another preferred embodiment the dosage is a single dosage per day of 50 milligrams, while in yet another preferred embodiment the dosage is a single dosage per day of 75 milligrams. In another preferred embodiment, the dosage is a single dosage per day of approximately 125 milligrams and in another preferred embodiment, the dosage is a single dosage per day of approximately 150 milligrams. In another preferred embodiment, the dosage is a single dosage per day of approximately 200 milligrams. Multiple dosage is also contemplated.

It is believed that oral administration of a purified enantiomer of flosequinan (e.g. the (+) flosequinan enantiomer) and pharmaceutical compositions comprising a purified enantiomer of flosequinan (e.g the (+) flosequinan enantiomer) is an effective mode of administration. In one embodiment, the enantiomer of flosequinan is introduced into the male or female orally. It is believed that an oral dosage of up to approximately 200 milligrams of a racemic mixture of flosequinan is an effective oral dosage. It is also believed that the oral administration of a purified enantiomer of flosequinan is effective at even lower dosages (e.g. less than 200 mg). While the present invention is not limited to a specific dosage level, in one embodiment, the male or female is an adult human and the oral dosage of a purified enantiomer of flosequinan is in a single dose per day of up to approximately two hundred milligrams, more preferably, between approximately fifty to approximately seventy-five milligrams. In an even more preferred embodiment, a purified enantiomer of flosequinan is administered in a single oral dose per day of between approximately twenty and approximately fifty, and even more preferably, between approximately ten and approximately twenty milligrams per day. Multiple dosage is also contemplated.

Flosequinan is water soluble and is soluble in many organic solvents. Thus, while the present invention is not limited by the form of oral administration, aqueous and organic solution of flosequinan for oral administration is contemplated. Likewise, flosequinan can be associated with a solid pharmaceutical carrier for solid oral administration (i.e., in pill form). One skilled in the art is able to readily prepare such solid formulations, and in one embodiment, the inactive ingredients include croscarmellose sodium, hydroxypropyl methylcellulose, lactose, magnesium stearate, methocel E5, microcrystalline cellulose, povidine, propylene glycol and titanium dioxide.

Oral administration of cilostazol is possible. While the present invention is not limited to a specific dosage level, a single dosage per day of 100 milligrams for adult humans is contemplated. Multiple dosage is also contemplated. In another embodiment, a dosage of less than 100 milligrams per day is contemplated (i.e., 25 to 75 milligrams). In another embodiment, two or three dosages per day, each of up to approximately 200 milligrams, are contemplated. In a preferred embodiment, two dosages per day, each of approximately fifty to approximately 100 milligrams of cilostazol are contemplated.

Peak plasma concentrations of cilostazol are observed 2–4 hours following oral administration (See e.g., Suri et al., J. Clin. Pharmacol. 38: 144–150 [1998]; Niki and Mori, Arzneimittelforschung 35: 1173–1185 [1985]).

While the present invention is not limited by the form of oral administration, aqueous and organic solutions of cilostazol for oral administration are contemplated. Likewise, cilostazol can be associated with a solid pharmaceutical carrier for solid oral administration. The compositions may be formulated in a manner known to one skilled in the art, using pharmaceutically acceptable carriers suitable for use in such compositions that are also well known in the art. It is contemplated that the compositions of the present invention comprise 0.1–90% by weight of cilostazol. In one embodiment, cilostazol can be prepared in tablet form by mixing cilostazol with an inert diluent such as lactose (See e.g., U.S. Pat. No. 5,627,191 to Birch et al., hereby incorporated by reference). In one preferred embodiment, cilostazol is administered as a tablet.

Flosequinan and cilostazol may also be administered cutaneously in a carrier adapted for topical administration. Such carriers include creams, ointments, lotions, pastes, jellies, sprays, aerosols, bath oils, or other pharmaceutical carriers which accomplish direct contact between flosequinan or cilostazol and the pore of the skin. In general pharmaceutical preparations may comprise from about 0.001% to about 10%, and preferably from about 0.01 to 5% by w/w of the active compound (e.g., flosequinan or cilostazol) in a suitable carrier. In some cases it may be necessary to dissolve the active compound in an appropriate solvent such as ethanol or DMSO (dimethylsulfoxide), and the like, to facilitate incorporation into a pharmaceutical preparation.

While the present invention is not limited by a specific method of introducing flosequinan or cilostazol by injection, injection of flosequinan or cilostazol can be carried out by any conventional injection means (e.g., employing an hypodermic syringe and needle or a similar device such as the NovolinPen, sold by Squibb-Novo, Inc., Princeton, N.J., USA). This injection may be by the subject injecting him or herself or by another person injecting the patient.

Flosequinan or cilostazol can be introduced by injection in a physiologically acceptable composition. Such compositions are aqueous solutions that are physiologically acceptable for administration by injection. The physiologically acceptable carrier is selected such that it is not painful or irritating upon injection. The physiologically acceptable compositions will preferably be sterile at the time of administration by injection.

Among the physiologically acceptable compositions for use in the methods is physiological saline or phosphate buffered saline, in which flosequinan or cilostazol is dissolved or suspended, such that the resulting composition is suitable for injection. Such a physiologically acceptable composition can also include a non-irritant preservative, such as, e.g., benzalkonium chloride at 0.05% (w/v) to 0./2% (w/v). As the skilled artisan will understand, there are numerous non-toxic salts of VIP, PHM and α-adrenergic blockers that can be employed in a physiologically acceptable composition for use in the methods herein, including, among others, the chloride, bromide, acetate, sulfate, and mesylate salts.

While the present invention is not limited to the method of injecting flosequinan or cilostazol, in the preferred embodiment, it is injected with a standard syringe. One skilled in the art would be capable of injecting flosequinan or cilostazol with a carrier as described above.

Other Compounds Useful in the Treatment of Gastroparesis

The invention is further directed to pyridinone compounds with therapeutic activity, and to therapeutic compositions containing such compounds, wherein the compounds have the general formula I:

(I)

$R_1$ is hydrogen, lower alkyl optionally substituted by hydroxy or $C_{1-4}$ alkoxycarbonyl, allyl, propynyl or phenyl-lower alkyl in which the phenyl ring is optionally substituted by 1 or 2 $C_{1-4}$ alkoxy groups;

$R_2$ is hydrogen or lower alkyl;

$R_3$ is $(X)_m$—$S(O)_nR_4$, $COR_5$, $SR_6$, or $S(OH)(O)NR_7$, wherein m is 0 or 1, n is 0, 1, or 2, X is oxygen or lower alkylene, $R_4$ is $C_{1-4}$ alkyl, $R_5$ is hydroxyl, lower alkyl carbonyl, amino, or lower alkyl amino, and $R_6$ and $R_7$ are lower alkyl; and ring A represents an optionally substituted phenyl ring of the formula:

wherein $R_8$, $R_9$ and $R_{10}$, which may be the same or different, are hydrogen, lower alkyl, lower alkoxy, lower alkanoyl, halo, tri-fluoromethyl, lower alkylthio, lower alkylsulphinyl, lower alkylsulphonyl, halogenated lower alkyl, halogenated lower alkoxy, cyano, phenyl, or phenyl substituted by 1 to 3 groups independently selected from lower alkyl, lower alkoxy and trifluoromethyl; or ring A represents an optionally substituted thiophene ring of the formula:

wherein $R_{11}$ is hydrogen, lower alkyl, lower alkoxy, lower alkanoyl, halo, trifluoromethyl, lower alkylthio, phenyl, or phenyl substituted by halogen, or a pharmaceutically acceptable salt thereof.

The compounds of the general formula I have been found to have antihypertensive activity and cardiac activity in warm-blooded animals. The compounds, methods of making the compounds, antihypertensive and cardiac therapeutic compositions of the compounds, and methods for treating hypertension and heart failure using the compounds are described in U.S. Pat. Nos. 4,302,460, 4,522,884, 4,855,291, 4,877,793, 4,710,506, 4,772,614 and 4,997,840, the disclosures of which patents are expressly incorporated herein, in their entirety, by reference.

In a preferred embodiment, the invention provides pharmaceutical compositions comprising compounds of the general formula I, and methods of using the compositions to treat subjects with symptoms of gastroparesis, such that said symptoms are reduced. As described above for flosequinan and cilostazol, the invention is not limited by the particular nature of the pharmaceutical composition, or by the method of introduction of the active or therapeutic compound to the body. All of the treatment methods and compositions contemplated above are also contemplated here for compounds of formula I. The active ingredient in the compositions is preferably administered in unit dosage form. In one embodiment, tablets and capsules may conveniently contain a unit dosage of the active compound of 1–500 mg/kg, more preferably 5–100 mg/kg and still more preferably 5–50 mg/kg.

The compounds of formula I may contain one or more asymmetric centers and, therefore, can exist as enantiomers or diastereoisomers. Furthermore, certain compounds of formula I containing alkenyl groups may exist as cis-isomers or trans-isomers. In each case, the invention includes both mixtures and separate individual isomers. The compounds of formula I may also exist in tautomeric forms and the invention includes both mixtures and separate individual tautomers.

Preferred compounds of the general formula I for use in the pharmaceutical compositions and methods of the invention are compounds having the general formulas II and III:

(II)

(III)

wherein $R_1$, $R_3$, $R_8$, $R_9$, $R_{10}$, and $R_{11}$ are defined as above.

With regard to compounds of formula II, still more preferred compounds have the formula IIA:

(IIA)

wherein $R_3$ is $(X)_m-S(O)_nR_4$, $COR_5$, $SR_6$, or $S(OH)(O)NR_7$; and

(a) $R_{10}$ is hydrogen and $R_9$ is 6-lower alkoxy, 8-lower alkoxy, 5-halo or 6-halo;

(b) $R_9$ is hydrogen and $R_{10}$ is halo; lower alkyl, lower alkoxy, trifluoromethyl or lower alkyl-thio;

(c) $R_{10}$ is halo, lower alkoxy or lower alkyl and $R_9$ is 6-lower alkyl, 6-lower alkoxy or 6-halo of a different value from $R_{10}$; or (d) $R_9$ and $R_{10}$ are hydrogen.

Preferred embodiments include compounds of formula IIA wherein $R_1$ and $R_2$ are methyl, $R_9$ is hydrogen and $R_{10}$ is halo, lower alkyl or trifluoromethyl. More preferably, $R_{10}$ is halo or $C_1$-$C_4$ alkyl. In yet another preferred embodiment, $R_9$ is 6-lower alkoxy and $R_{10}$ is halo or lower alkoxy. In a further preferred embodiment, $R_9$ is 6-halo and $R_{10}$ is lower alkoxy. In another preferred embodiment, $R_{10}$ is $C_1$-$C_4$ alkyl. Thus, preferred embodiments include compounds of formula IIB, IIC, IID, IIE, IIF, IIIA and IIIB as follows:

(IIB)

(IIC)

(IID)

(IIE)

(IIF)

(IIIA)

-continued (IIIB)

Preferred compounds of formula IIB are those in which m is 1, n is 2, and X is oxygen. Preferred compounds of formula IIC include those in which m is 0, n is 1 or 2, and $R_4$ is methyl. Preferred compounds of formula IID include those in which $R_5$ is amino or lower alkyl amino. Preferred compounds of formula IIE include those in which $R_6$ is methyl. Preferred compounds of formula IIF include those in which $R_7$ is methyl. Preferred compounds of formula IIIA include those in which n is 1 and $R_4$ is methyl. Preferred compounds of formula IIIB include those in which $R_5$ is amino or lower alkyl amino.

Specific preferred compounds of these formulae include: 1-methyl-3-methylsulphinyl-4-quinolone, 7-fluoro-1-methyl-4-oxo-1,4-dihydro-quinolone-3 -carboxamide, 4-methyl-7-oxo-4,7-dihydrothieno[3,2-b]pyridine-6-carboxamide, 4-methyl-6-methylsulphinyl-7(4H1)-thieno[3,2-b]pyridinone, 7-chloro-1-methyl-3 -methylsulphamoyl-4-quinolone, 1-methyl-4-oxo-1,4-dihydroquinol-3-yl methanesulphonate, 7-chloro-1-methyl-4-oxo-1,4-dihydroquinoline-3-carboxamide, 7-fluoro-1 -methyl-3-methylsulphonyl-4-quinolone, or 7-fluoro-1-methyl-3-methylthio-4-quinolone, or pharmaceutically acceptable salts thereof.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); L (liters); ml (milliliters); μl (microliters); cm (centimeters); mm (millimeters); μm (micrometers); nm (nanometers); ° C. (degrees Centigrade).

EXAMPLE 1

A recent article demonstrated the ability of sildenafil (a PDE5 inhibitor) to reverse delayed gastric emptying in diabetic (NOD (non obese diabetic)-diabetic and toxin induced-diabetic) mice. This effect is hypothesized to compensate for the reduced nNOS (neuronal nitric oxide synthase) gene expression observed in the diabetic animals. [Watkins, CC et al. "Insulin restores neuronal nitric oxide synthase expression and function that is lost in diabetic gastropathy" *J Clin Invest* 106:373–384 (2000)]. Although these results are noted to have potential therapeutic applications in the management of diabetic gastropathy in humans, sildenafil citrate has a lack of specificity for its target, enzyme phosphodiesterase 5 (PDE5), and exerts a definite inhibition on the enzyme phosphodiesterase 6 (PDE6), located in the retina. It has been shown that the inhibition of PDE6 results in color vision defects as a side effect of treatment with sildenafil citrate. Furthermore, side effects such as flushing, headache, nasal congestion, and dyspepsia (heartburn) have also been associated with sildenafil citrate treatment of impotence. [Moreira et al., "Side-effect profile of sildenafil citrate (Viagra) in clinical practice," *Urology,* 56(3): 474-76 (2000)].

In this example, a biochemical assay was performed to test the percentage of phosphodiesterase 6 (PDE6) inhibition of various molar concentrations of sildenafil citrate (Viagra) as compared to that of a 100 μM concentration of a racemic mixture of flosequinan as follows.

PDE6 partially purified from bovine retinal rod and activated by trypsin was used. In four separate reactions, Viagra at molar concentrations of 0.3 μM, 1.0 μM, and 3.0 μM, and a 100 μM racemic mixture of flosequinan were incubated with 0.2 μ/ml active PDE6 and 100 μM cGMP containing 0.1 μM [$^3$H]cGMP in Tris buffer pH 7.5 for 20 minutes at 30° C. Each reaction was terminated by raising the temperature to 100° C. for 2 minutes. The resulting GMP was converted to guanosine by addition of 10 mg/ml snake venom nucleotidase and further incubated at 30° C. for 10 minutes. Unhydrolyzed cGMP was bound to AGI-X2 resin, and [$^3$H]guanosine remaining in the aqueous phase was quantitated by scintillation counting.

The results of the assays, as noted in the table below, indicate that although Viagra inhibits PDE6 around 50% at concentrations as low as 0.3 μM, such levels of inhibition of PDE6 require greater than 100 μM amounts of flosequinan (i.e. more than 300 times more compound on a molar basis). These empirical results could not be predicted.

| Compound | Concentration | % Inhibition of PDE6 |
|---|---|---|
| Viagra | 3.0 μM | 87 |
| Viagra | 1.0 μM | 62 |
| Viagra | 0.3 μM | 57 |
| Flosequinan | 100 μM | 36 |

EXAMPLE 2

Figure 2:
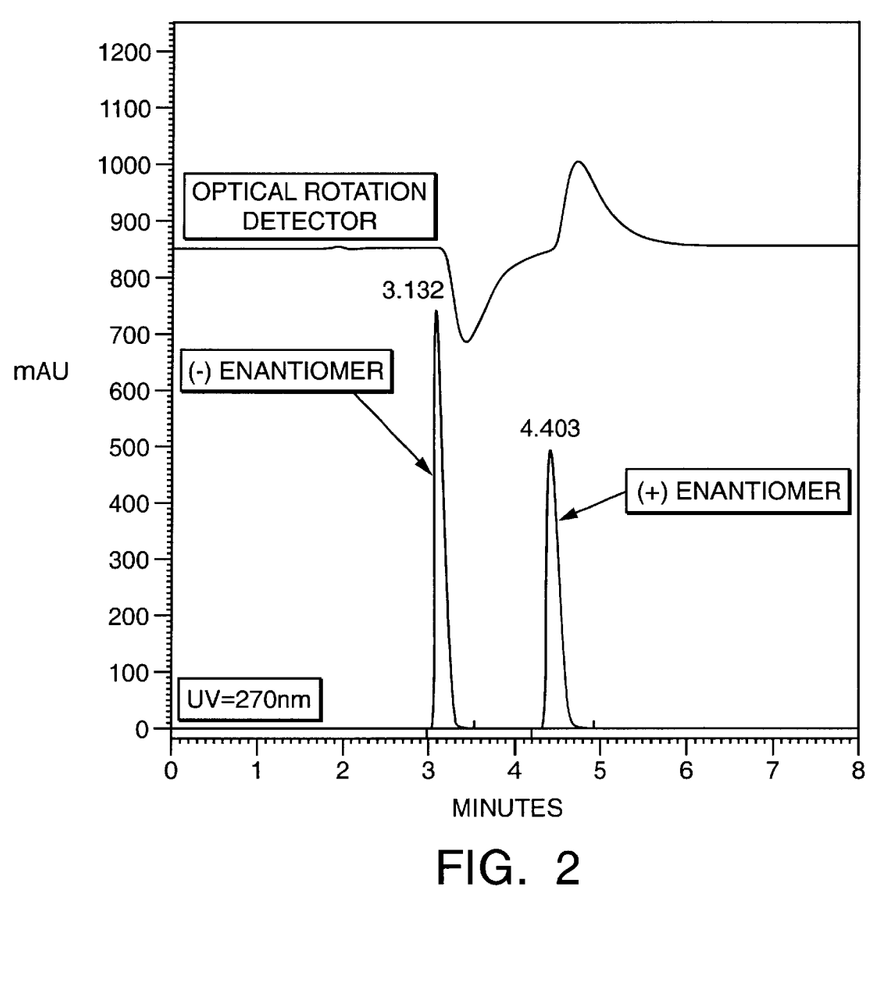
FIG. 2 depicts the respective HPLC column retention times and optical rotations of the enantiomers of flosequinan separated by the method provided in Example 2.

In this example, the enantiomers of flosequinan were resolved by high- performance liquid chromatography (HPLC) as follows. A 5.0 g sample of a racemic mixture of flosequinan was resolved over a 10 cm IDx50 cm L CHIRALCEL OD HPLC column (Chiral Technologies, Exton, Pa.) at 25° C. and with a flow rate of 1.0 ml/minute such that the column pressure was 37 bar. The mobile phase employed was 100% methanol and the detection of the mixture was performed at 270 nm. The (−) enantiomer had a retention time of 3.13 minutes, while the (+) enantiomer had a retention time of 4.40 minutes. A total of 2.1 g of the (−) enantiomer having an optical purity greater than 99% was produced. A total of 2.3 g of the (+) enantiomer having an optical purity greater than 99% was produced. (See, FIG. 2).

EXAMPLE 3

In this example, a racemic mixture of flosequinan and the (+) and (−) enantiomers of flosequinan were subjected to biochemical enzyme assays to determine their respective percent inhibition of a variety of phosphodiesterases (PDE1-PDE6). The reaction conditions for each PDE assay were as follows. PDE1: PDE1 partially purified from bovine heart was used. A racemic mixture of flosequinan, and each enantiomer of flosequinan, all at a molar concentration of 100 μM, were independently incubated with 13 μg PDE1 enzyme, 1.0 μM [$^3$H]cAMP and CaCl$_2$/calmodulin in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE2: PDE2 partially purified from human platelets was used. A racemic mixture of flosequinan, and each enantiomer of flosequinan, all at a molar concentration of 100 μM, were independently incubated with 23 μg PDE2 enzyme, 25 μM cAMP containing 0.05 μM [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE3: PDE3 partially purified from human platelets was used. A racemic mixture of flosequinan, and each enantiomer of flosequinan, all at a molar concentration of 100 μM, were independently incubated with 13 μg PDE3 enzyme and 1 μM cAMP containing 0.01 μM [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE4: PDE4 partially purified from human U-937 pronocytic cells was used. A racemic mixture of flosequinan, and each enantiomer of flosequinan, all at a molar concentration of 100 μM, were independently incubated with 20 μg PDE4 enzyme and 1 μM cAMP containing 0.01 μM [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE5: PDE5 partially purified from human platelets was used. A racemic mixture of flosequinan, and each enantiomer of flosequinan, all at a molar concentration of 100 μM, were independently incubated with 120 μg PDE5 enzyme and 1 μM cGMP containing 0.01 μM [$^3$H]cGMP in Tris buffer pH 7.5 for 20 minutes at 30° C. The reaction was terminated by boiling for 2 minutes, and the resulting GMP was converted to guanosine by addition of 10 mg/ml snake venom nucleotidase and further incubation at 30° C. for 10 minutes. Unhydrolyzed cGMP was bound to AGI-X2 resin, and the remaining [$^3$H]guanosine in the aqueous phase was quantitated by scintillation counting.

PDE6: PDE6 partially purified from bovine retinal rod and activated by trypsin was used. A racemic mixture of flosequinan, and each enantiomer of flosequinan, all at a molar concentration of 100 μM, were independently incubated with 0.2 μg/ml active PDE6 and 100 μM cGMP containing 0.1 μM [$^3$H]cGMP in Tris buffer pH 7.5 for 20 minutes at 30° C. Each reaction was terminated by boiling for 2 minutes. The resulting GMP was converted to guanosine by addition of 10 mg/ml snake venom nucleotidase, and further incubated at 30° C. for 10 minutes. Unhydrolyzed cGMP was bound to AGI-X2 resin, and [$^3$H]guanosine remaining in the aqueous phase was quantitated by scintillation counting.

The results of the above PDE assays are presented in the following table. The (+) enantiomer of flosequinan demonstrated more PDE1 and PDE3 inhibitory activity when compared with the (−) enantiomer of flosequinan. These empirical results could not be predicted.

| Target Phosphodiesterase | % Inhibition w/ 100 μM racemic mixture of flosequinan | % Inhibition w/ 100 μM (+)- flosequinan | % Inhibition w/ 100 μM (−)- flosequinan |
|---|---|---|---|
| PDE1 | 31 | 28 | 11 |
| PDE2 | 18 | 18 | 13 |
| PDE3 | 26 | 32 | 5 |
| PDE4 | 24 | 6 | 1 |
| PDE5 | 11 | 17 | 10 |
| PDE6 | 21 | 22 | 21 |

EXAMPLE 4

This example describes how certain preferred compounds of general formula (I) can be prepared.

a. 7-fluoro-1-methyl-4-oxo-1,4-dihydroquinolone-3-carboxamide can be prepared as described in Example 1 of U.S. Pat. No. 4,855,291.
  (i) A mixture of ethyl 7-fluoro-4-hydroxyquinoline-3-carboxylate (4.7 g), anhydrous potassium carbonate (3.0 g), dimethyl sulphate (2.52 g) and butanone (200 ml) can be boiled under reflux for 14 hours. The solvent can be evaporated and the residue can be triturated with dichloromethane (150 ml). The mixture can be filtered and the filtrate evaporated to a small volume. Diethyl ether can be added, causing a solid to precipitate. The solid can be collected, washed with ether, dried and recrystallised from industrial methylated spirit to give the compound ethyl 7-fluoro-1-methyl-4-oxo-1,4-dihydroquinoline-3-carboxylate, m.p. 164° C.–166° C.
  (ii) A mixture of 19.0 g of the above carboxylate ester, aqueous ammonia (specific gravity 0.88, 750 ml) and capryl alcohol (2 drops) can be stirred on a steam bath for 1.5 hours, then cooled to room temperature. The solid product can be collected by filtration and recrystallised from industrial methylated spirit/water 3:2 to give the compound 7-fluoro-1-methyl-4-oxo-1,4-dihydroquinoline-3-carboxamide, m.p. 317° C.–318° C.

b. 4-methyl-7-oxo-4,7-dihydrothieno[3,2-b]pyridine-6-carboxamide can be prepared as described in Example 1 of U.S. Pat. No. 4,877,793.
  (i) Dimethyl sulphate (3.9 ml) can be added to a stirred solution of ethyl 7-hydroxythieno[3,2-b]-pyridine-6-carboxylate (4.63 g) and potassium hydroxide (3.5 g) in water (50 ml) at 0° C.–5° C. More water (20 ml) can be added and the mixture can be stirred at ambient temperature for 24 hours. The solid product can be collected by filtration, washed with water and dried to give the compound ethyl 4-methyl-7-oxo-4,7-dihydrothieno[3,2-b]pyridine-6-carboxylate, m.p. 122° C.–128° C.
  (ii) A mixture of 3.0 g of the product from (i) above and aqueous ammonia (specific gravity 0.880, 60 ml) can be stirred and heated on a steam bath. Effervescence will occur and octan-1-ol (2 ml) and more aqueous ammonia (specific gravity 0.880, 20 ml) can be added and heating on the steam bath can be continued overnight. The mixture can then be cooled to ambient temperature and the solid product collected by filtration, dried and crystallised from industrial methylated spirit to give the compound 4-methyl-7-oxo-4,7-dihydrothieno[3,2-b]pyridine-6-carboxamide, m.p. 255° C.–258° C.

c. 4-methyl-6-methylsulphinyl-7(4H)-thieno[3,2-b] pyridinone can be prepared as described in Example 2 of U.S. Pat. No. 4,710,506.

A solution of 3-chloroperbenzoic acid (85%; 1.63 g) in dichloromethane (60 ml) can be added dropwise during 20 minutes to a stirred solution of 4-methyl-6-methylthiothieno [3,2-b]pyrid-7(4H)-one (2.0 g) in dichloromethane (60 ml) at 0° C.–5° C. After 4 hours, more 3-chloroperbenzoic acid (0.15 g) in dichloromethane (10 ml) can be added and the mixture stirred overnight at ambient temperature. More 3-chloroperbenzoic acid (0.15 g) in dichloromethane (10 ml) can be added and the mixture can again be stirred overnight at ambient temperature. The resulting solution can be extracted with saturated aqueous sodium bicarbonate solution (5×150 ml) and saturated aqueous sodium chloride solution (1×150 ml) and the organic phase can be discarded. The aqueous extracts are combined and extracted with dichloromethane (5×100 ml). The organic extracts are combined, dried over anhydrous magnesium sulphate and evaporated to give a solid product. This product can be crystallised from industrial methylated spirit to give the compound 4-methyl-6-methylsulphinylthieno [3,2-b]pyrid-7(4H)-one, m.p. 174° C.–176° C.

d. 7-chloro-1-methyl-3-methylsulphamoyl-4-quinolone can be prepared as described in Example 4 of U.S. Pat. No. 4,772,614.

(i) 7-Chloro-1-methyl-4-quinolone (6.9 g) and chlorosulphonic acid (14 ml) can be stirred and heated at 140° C. for 2 hours. The reaction mixture can be cooled to room temperature and carefully added dropwise to ice water (200 ml). The solid which forms can be collected, washed with water and dried in air to give the compound 7-chloro-1-methyl-4-oxo-1,4-dihydroquinoline-3-sulphonyl chloride, m.p. >300° C.

(ii) 6.5 g of the above sulphonyl chloride and aqueous methylamine (30% w/v; 220 ml) can be stirred at room temperature for 3 hours. The resulting solid can be collected, washed with water and crystallised from dichloromethane/industrial methylated spirit 1:1. The product can be collected and partitioned between water (200 ml) and dichloromethane (200 ml). The organic layer can be separated, dried over anhydrous sodium sulphate and evaporated to dryness. The residue can be crystallised from industrial methylated spirit to give the compound 7-chloro-1, N-dimethyl-4-oxo-1,4-dihydroquinoline-3-sulphonamide, m.p. 220° C.–223° C.

e. 7-chloro-1-methyl-4-oxo-1,4-dihydroquinoline-3--carboxamide can be prepared as described in Example 4 of U.S. Pat. No. 4,855,291.

A mixture of ethyl 7-chloro-1-methyl-4-oxo-1,4-dihydroquinoline-3-carboxylate (5.0 g) and aqueous ammonia (specific gravity 0.88, 100 ml) can be stirred and heated on a steam bath for 3.5 hours. More aqueous ammonia (100 ml) can be added and heating continued for a further 21 hours. The mixture can be cooled in ice. The solid product can be collected by filtration and dried to give the compound 7-chloro-1-methyl-4-oxo-1,4-dihydroquinoline-3-carboxamide, m.p. >240° C.

From the above, it should be clear that the present invention provides methods of treatment of symptoms of gastroparesis with pharmaceutical agents. In particular, quinolinones are administered therapeutically to patients having such symptoms.

What is claimed is:

1. A method of treating the symptoms of gastroparesis,
   a) providing:
      in a subject in need thereof comprising administering an effective amount of a formulation comprising flosequinan to said subject so
   b) that said symptoms of gastroparesis are reduced, wherein said subject is free of symptoms of cardiac disease and has not been treated with one or more drugs that cause hypotensive effects.

2. The method of claim 1, wherein said flosequinan is present as a racemic mixture.

3. The method of claim 1, wherein said flosequinan is a purified enantiomer.

4. The method of claim 1, wherein said flosequinan is introduced into said subject by oral administration.

5. The method of claim 4, wherein said subject is an adult human and said oral administration comprises up to approximately 200 milligrams of flosequinan.

6. The method of claim 1, wherein said flosequinan is introduced into said subject cutaneously.

7. The method of claim 1, wherein said subject is a female.

8. The method of claim 7, wherein said female has diabetes.

9. The method of claim 1, wherein said subject is a male.

10. The method of claim 9, wherein said male has diabetes.

11. A method of treating the symptoms of gastroparesis,
    a) providing:
       in a subject in need thereof comprising administering an effective amount of a formulation comprising cilostazol to said subject so
    b) that said symptoms of gastroparesis are reduced, wherein said subject is free of symptoms of cardiac disease and has not been treated with one or more drugs that cause hypotensive effects.

12. The method of claim 11, wherein said cilostazol is introduced into said subject by oral administration.

13. The method of claim 12, wherein said subject is an adult human and said oral administration comprises up to approximately 100 milligrams of cilostazol.

14. The method of claim 11, wherein said cilostazol is introduced into said subject cutaneously.

15. The method of claim 11, wherein said subject is a female.

16. The method of claim 15, wherein said female has diabetes.

17. The method of claim 11, wherein said subject is a male.

18. The method of claim 17, wherein said male has diabetes.

* * * * *